United States Patent
Saito et al.

(10) Patent No.: US 7,951,584 B2
(45) Date of Patent: May 31, 2011

(54) METHOD FOR PRODUCTION OF BIOLOGICAL ORGANIC MATERIAL AND CULTURE VESSEL

(75) Inventors: Nagahiro Saito, Nagoya (JP); Osamu Takai, Nagoya (JP); Yunying Wu, Nagoya (JP); Hiroyuki Honda, Nagoya (JP); Akira Ito, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 83 days.

(21) Appl. No.: 11/909,909

(22) PCT Filed: Mar. 29, 2006

(86) PCT No.: PCT/JP2006/306498
§ 371 (c)(1),
(2), (4) Date: Jan. 26, 2009

(87) PCT Pub. No.: WO2006/106748
PCT Pub. Date: Oct. 12, 2006

(65) Prior Publication Data
US 2009/0197333 A1  Aug. 6, 2009

(30) Foreign Application Priority Data

Mar. 30, 2005 (JP) .................................. 2005-099509
Aug. 25, 2005 (JP) .................................. 2005-244946

(51) Int. Cl.
*C12M 1/12* (2006.01)
(52) U.S. Cl. ................. 435/297.1; 435/297.5; 435/299.1
(58) Field of Classification Search ........................ None
See application file for complete search history.

(56) References Cited

U.S. PATENT DOCUMENTS

| | | | |
|---|---|---|---|
| 6,464,983 B1 * | 10/2002 | Grotendorst | 424/198.1 |
| 7,201,831 B2 * | 4/2007 | Vincent | 204/416 |
| 2005/0195245 A1 | 9/2005 | Yamada et al. | |
| 2008/0032403 A1 | 2/2008 | Saito et al. | |

FOREIGN PATENT DOCUMENTS

| | | | |
|---|---|---|---|
| JP | 64067184 | | 3/1989 |
| JP | 11304666 | | 11/1999 |
| JP | 2004254622 | | 9/2004 |
| JP | 2004267562 | | 9/2004 |
| JP | 2005249436 | | 9/2005 |
| JP | 2006088034 | | 4/2006 |
| JP | 2006217808 | | 8/2006 |
| WO | 2004/011938 | | 2/2004 |
| WO | WO2004/011938 | * | 2/2004 |
| WO | 2006028274 | | 3/2006 |

OTHER PUBLICATIONS

Written Opinion For PCT/JP2006/306498 Mailed Jul. 11, 2006.
International Search Report for PCT/JP2006/306498 dated Jul. 11, 2006.
British Office Action for GB20070018648 mailed on May 12, 2010.
Japanese Office Action dated Aug. 5, 2010 corresponding to U.S. Appl. No. 11/909,909, filed Jan. 26, 2009.

* cited by examiner

*Primary Examiner* — James S Ketter
(74) *Attorney, Agent, or Firm* — Turocy & Watson, LLP

(57) ABSTRACT

Disclosed is a method for producing a biological organic material in a liquid droplet comprising a culture medium composed of specified ingredient. The method comprises the steps of: providing a substantially spherical liquid droplet on a substrate in an unadhered state, the substrate preferably having such a water-repellent surface that the water contact angle becomes 150° or greater; and culturing a biological organic material in the liquid droplet.

16 Claims, 12 Drawing Sheets

(A)

(B)

100 μm

200 μm

100 μm 1.0mm

100 μm

100 μm

100 μm

100 μm

500 μm

200 μl

200 μl

METHOD FOR PRODUCTION OF BIOLOGICAL ORGANIC MATERIAL AND CULTURE VESSEL

TECHNICAL FIELD

The present invention relates to a method for producing a biological organic material such as cells or tissue, and more particularly to a method that includes culturing a predetermined biological organic material in a liquid droplet.

The present international application claims priority to Japanese Patent Application No. 2005-099509 filed on Mar. 30, 2005, and Japanese Patent Application No. 2005-244946 filed on Aug. 25, 2005, and incorporates by reference the entire contents of these applications.

BACKGROUND ART

Development of technology for culturing target cells or tissue, while maintaining the normal form and functions thereof, is indispensable for advancing the so-called regenerative medicine. Thus, development of tissue engineering that reproduces the target tissue by systematic culturing of cells is especially anticipated.

One of the tasks in the field of tissue engineering is to establish a method for spatially culturing (three-dimensionally culturing) cells (in particular ES cells or other stem cells) or cell masses (including partially ordered aggregates; same hereinbelow) in a state in which a function of differentiating (aggregating) into a target tissue or organ is maintained, and also a culture vessel that is suitable for such method. With a general two-dimensional culturing method, for example, a method for culturing cells or tissue on a planar Petri dish, the cultured material is affected by gravity and easily assumes the form of a thin sheet, and such method is unsuitable for culturing a tissue that is wished to function properly in an organism that is a three-dimensional environment.

Further, establishing a method for culturing stem cells and cell masses (three-dimensional culturing method) and a culture vessel therefore are also important in terms of clarifying the mechanism of differentiation (aggregation) of ES cells (embryonic stem cells) and other stem cells. In particular, because most of the animal cells are adherent cells, long-term culturing in a floating state is difficult to perform by the conventional methods.

Conventionally, three-dimensional culturing of cells of this kind has been conducted by using a variety of culture carriers such as glass beads, metal chips, and inorganic porous materials (Japanese Patent Application Laid-open No. 2004-267562). However, these carriers are limited to those that do not inhibit multiplication of target cells (tissue). In addition, the configuration of culture device is made complex. Further, in three-dimensional culturing using a carrier, the carrier and culture are difficult to separate and culturing large quantities of cells and tissue having identical form and functions is generally difficult.

On the other hand, a hanging drop method (HD method) is a conventional method that uses no carrier. With the HD method, a culture medium has a semispherical shape, thereby making it possible to cause contact and aggregation of cells in the culture medium and form a three-dimensional cell mass. However, semispherical culture medium that can be formed by the HD method are limited to a small size. Further, the HD method requires cautious operations, and the culturing success ratio is not more than about 60% even for a skilled operator.

A method using a vessel with a U-shaped bottom (typically a U-bottom multiwell plate) that is subjected to appropriate surface treatment to reduce adhesion of cells involves operations that are simpler than those of the HD method. For example, Japanese Patent Application Laid-open No. 2004-254622 describes a culture vessel with a U-shaped bottom that is modified to be suitable for culturing ES cells, this method being an improvement over the aforementioned method. However, when culturing is performed using such a vessel with a U-shaped bottom, the cell mass is difficult to form and the culturing interval increases (that is, the growth rate of culture cells is low).

DISCLOSURE OF THE INVENTION

Accordingly, the present invention was created to resolve the aforementioned problems inherent to the conventional technology for three-dimensional culturing, and it is an object of the present invention to provide a culture vessel suitable for culturing a biological organic material (cells, cell mass, differentiated tissue, etc.) of desired properties in a simple manner and at a high rate. Another object of the present invention is to provide a method for producing the target biological organic material with good efficiency by using the vessel.

One of the methods provided by the present invention is a method for producing a biological organic material in a liquid droplet comprising a culture medium containing predetermined components. This method comprises disposing a substantially spherical liquid droplet in a non-fixed state on a substrate having a water-repellent surface and culturing the biological organic material in the liquid droplet.

In the present specification, "biological organic material" is a general term indicating a culturable organic material constituting a living body. Thus, various cells (stem cells, body cells, reproductive cells, etc.) and tissues (including cell mass generated during culturing or differentiated tissue) sampled from people, other animals, vegetables, and microorganisms are included in the biological organic material.

With the production method in accordance with the present invention, a liquid droplet of a desired composition (for example, a buffer solution such as normal saline solution, a culture medium with a pH close to 7) is disposed on a water-repellent surface formed on a predetermined substrate. With this method, the surface where the liquid droplet is disposed is a water-repellent surface (that is, super-repellent surface). Therefore, the liquid droplet can maintain a substantially spherical (or perfectly spherical) shape. With the method disclosed herein, the target biological organic material is cultured in this spherical liquid droplet. With the method disclosed herein, the spherical liquid droplet provides a three-dimensional environment advantageously suitable for culturing a biological organic material. As a result, a biological organic material in which the desired state (for example, state after differentiation), functions, and phenotype are maintained can be cultured and produced without using the above-described carrier. Further, by increasing the number of liquid droplets used, it is possible to manufacture a large quantity of identical biological organic materials with a simple configuration.

It is preferred that culturing be performed in a liquid droplet in a state in which a gas can be supplied to the portion immediately below the liquid droplet. By using as a culturing field a substantially spherical liquid droplet disposed in an environment in which gas exchange can be easily conducted, it is possible to enhance multiplication and differentiation, for example, of a variety of stem cells (embryonic stem cells (ES cells), mesenchymal stem cells (MSC), hematopoietic stem cells, hepatic stem cells, and various other somatic stem cells). Further, a state after differentiation induction can be maintained and a cell mass (cluster) and tissue with desired properties can be obtained. For example, with the method disclosed herein, differentiation from stem cells such as MSC and ES cells to cartilage cells (or osteoblastic cells) can be performed and a cartilage tissue (or bone tissue) can be formed.

Therefore, the present invention according to another aspect thereof provides a method for producing a differentiated biological organic material derived from stem cells, this method comprising forming a substantially spherical liquid droplet on a substrate having a water-repellent surface capable of holding the liquid droplet in a substantially spherical state, culturing a stem cell of at least one kind in the liquid droplet in a state in which a gas can be supplied to a portion immediately below the liquid droplet, and differentiating the stem cell in the liquid droplet. In a preferred mode, the differentiated biological organic material derived from a stem cell is a cartilage cell and/or cartilage tissue.

In another preferred mode of the method disclosed herein the water-repellent surface comprises a water-repellent layer formed of a compound having a hydrophobic moiety formed on the surface of the substrate. By forming the water-repellent surface from a water-repellent layer (preferably, a monomolecular layer) composed of a predetermined compound, it is possible to obtain a substantially constant thickness of the water-repellent surface (water-repellent layer) in a predetermined zone where the liquid droplet can be actually disposed and attain uniform water repellent performance.

In still another preferred mode of the method disclosed herein, a volume of the liquid droplet is at least 200 μL. By using a liquid droplet with a volume of 200 μL or more (the upper limit can differ depending on viscosity of the liquid constituting the liquid droplet; for example 200 μL to 1000 μL), it is possible to produce the desired biological organic material with good efficiency.

In a further preferred mode of the method disclosed herein, the biological organic material cultured in the liquid droplet is a stem cell of at least one kind and/or a cell or tissue differentiated from the stem cell (including the stage of a cell mass formed by aggregated cells). With such method, it is possible to enhance multiplication and differentiation, for example, of a variety of stem cells (embryonic stem cells (ES cells), mesenchymal stem cells (MSC), hematopoietic stem cells, hepatic stem cells, and various other somatic stem cells). Further, a state after differentiation induction can be maintained and a cell mass (cluster) and tissue with desired properties can be obtained. For example, with the method disclosed herein, differentiation from stem cells such as MSC and ES cells to cartilage cells (or osteoblastic cells) can be performed and a cartilage tissue (or bone tissue) can be formed.

Therefore, the present invention provides a method for producing a differentiated biological organic material derived from stem cells, the method comprising disposing a substantially spherical liquid droplet in a non-fixed state on a substrate having a water-repellent surface, culturing a stem cell of at least one kind in the liquid droplet, and differentiating the stem cell in the liquid droplet. In a still further preferred mode, the differentiated biological organic material derived from a stem cell is a cartilage cell and/or cartilage tissue.

With the method disclosed herein, liquid drop culturing can be performed in a variety of modes according to the properties of the biological organic material that is the object of production. In a still further preferred mode, a biological organic material can be cultured in a state in which the liquid droplet is stationary disposed on the water-repellent surface. In yet another preferred mode the biological organic material can be cultured, while continuously or intermittently moving the liquid droplet on the water-repellent surface (typically, while causing the liquid droplet to roll or slide on the water-repellent surface).

The present invention also provides a culture vessel for use in production of a biological organic material in a liquid droplet comprising a culture medium containing predetermined components, the culture vessel comprising a liquid droplet disposition portion configured of a water-repellent surface where a substantially spherical liquid droplet can be disposed in a non-fixed state. It is preferred that the culture vessel further comprise a circumferential wall or partition portion provided around of the liquid droplet disposition portion to prevent the liquid droplet from flowing out to the outside of the liquid droplet disposition portion.

With the culture vessel disclosed herein, because the substrate surface is water repellent (super-repellent), a liquid droplet of a substantially spherical shape can be formed and disposed on the substrate by dropping a culture medium (for example, including a variety of buffer solutions such as normal saline solution). The substantially spherical liquid droplet provides a three-dimensional environment advantageous for culturing biological organic materials. As a result, an almost spherical (preferably perfectly spherical) liquid droplet of a desired size can be formed in an easy manner and a desired biological organic material can be three-dimensionally cultured in an easy manner in the liquid droplet, without performing complex operation such as in the conventional HD method. By using such a vessel, it is possible to implement advantageously any of the methods for producing a biological organic material that are disclosed herein.

It is preferred that the culture vessel comprise a substrate formed so that a gas can be supplied immediately below a liquid droplet disposed in the liquid droplet disposition portion, and that at least a surface of the substrate that can come into contact with the liquid droplet has water repellency (that is, super-repellency) capable of holding the liquid droplet in a substantially spherical state thereof.

With such configuration, a gas (typically, air) can be supplied (caused to be present) immediately below the substantially spherical liquid droplet disposed on the substrate. Therefore, by contrast with the culturing process using the conventional U-bottom multiwell plate, gas exchange with the liquid droplet (culture) can be intensively performed even from the lower surface (bottom) of the liquid droplet disposed in a predetermined position. As a result, with the culture vessel of this mode, multiplication or growth of the biological organic material in the liquid droplet placed in an atmosphere with excellent gas exchange can be accelerated. Therefore, the production efficiency of the desired biological organic material (for example, a cell mass or aggregated fragments) can be increased.

In a still further preferred mode of the culture vessel disclosed herein, is formed a ventilation hole that can supply a gas immediately below the liquid droplet disposed in the liquid droplet disposition portion. Due to the presence of the ventilation hole immediately below the liquid droplet held in the predetermined position, gas exchange efficiency of the liquid droplet can be increased.

In yet another preferred mode of the culture vessel disclosed herein, a plurality of protruding portions arranged with a predetermined spacing and having the water-repellent surface are formed on the substrate, and configuration is made so that the liquid droplet is disposed on the plurality of protruding portions in a state in which the lowermost portion of the liquid droplet is floating above the substrate. Especially preferred is a culture vessel configured so that a volume of a liquid droplet that can be disposed on the protruding portions is at least 100 μL.

By disposing a liquid droplet on a substrate in a state in which the liquid droplet is supported by several protruding portions (that is, in a state in which the lowermost portion of the liquid droplet is floating above the substrate), it is possible to reduce further the contact surface area of the liquid droplet and the vessel (substrate). Therefore, culturing can be performed in the liquid droplet with excellent gas exchange and good production efficiency.

In yet another preferred mode of the culture vessel disclosed herein, the substrate comprises a mesh portion having a water-repellent surface capable of holding the liquid droplet in a substantially spherical state thereof, and configuration is made so that when the liquid droplet is disposed on the mesh portion, the lowermost portion of the liquid droplet is disposed in a gap portion of the mesh portion.

By disposing a substantially spherical liquid droplet on a mesh portion having a water-repellent surface, it is possible to reduce further the contact surface area of the liquid droplet and the vessel (substrate). Therefore, culturing can be performed in the liquid droplet with excellent gas exchange and good production efficiency.

In an especially preferred mode of the culture vessel disclosed herein, the water-repellent surface is configured of a water-repellent layer comprising a compound having a hydrophobic moiety. By forming the water-repellent surface from a water-repellent layer (preferably, a monomolecular layer) composed of a predetermined compound, it is possible to obtain a substantially constant thickness of the water-repellent surface (water-repellent layer) in a predetermined zone where the liquid droplet can be actually disposed and attain uniform water repellent performance.

BRIEF DESCRIPTION OF THE DRAWINGS

FIG. 7(A) is a planar view and FIG. 7(B) is a side view.

BEST MODE FOR CARRYING OUT THE INVENTION

Figure 1:
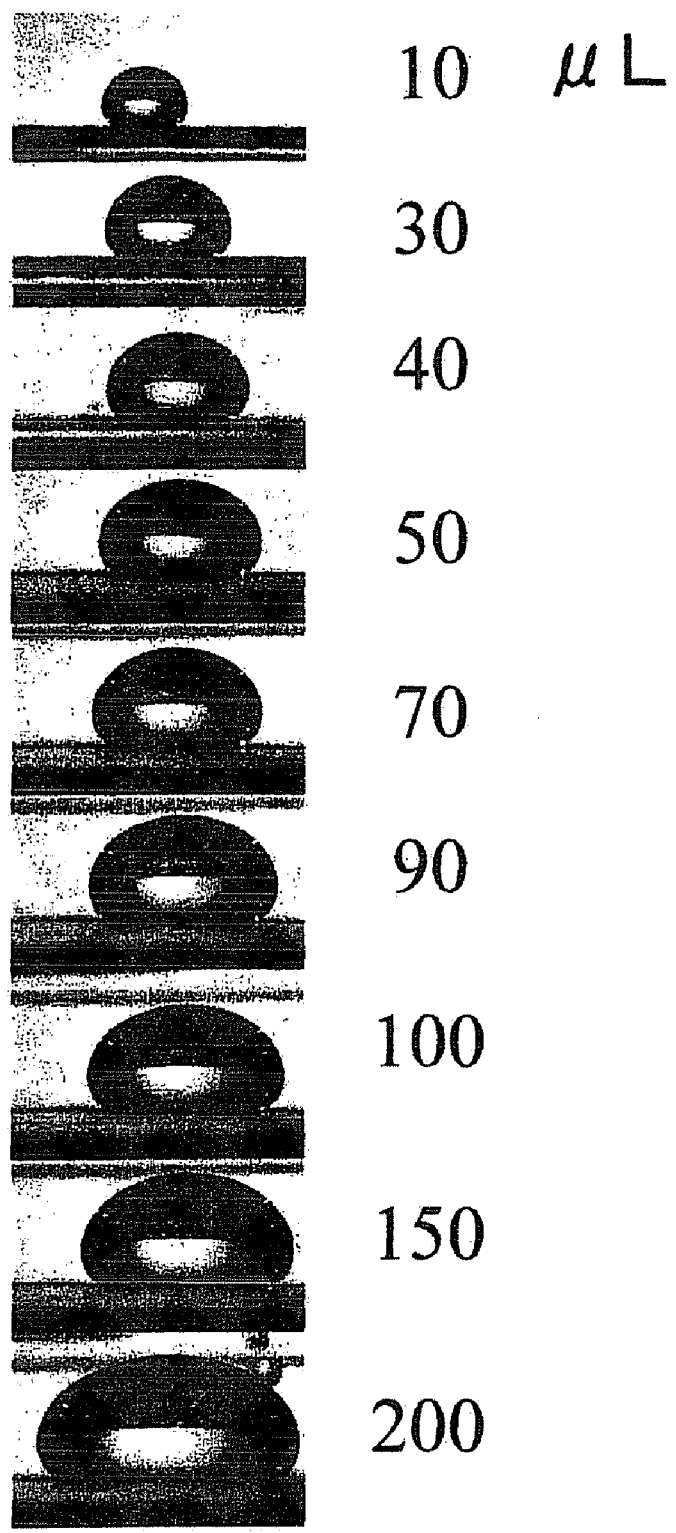
FIG. 1 is a photo illustrating substantially spherical liquid droplets (volume 10, 30, 40, 50, 70, 90, 100, 150, 200 μL) disposed on a water-repellent surface.

The preferred embodiment of the present invention will be described below. In the present specification, matters (for example, methods for procuring a culture medium or a biological organic material to be cultured) that are necessary for carrying out the present invention and other than those features (for example, the shape of the culture vessel (substrate), configuration of the water-repellent surface, method for forming the water-repellent surface, and method for culturing a biological organic material in a liquid droplet) that are specifically discussed in the present specification can be construed as matters of design based on the conventional technology in the pertinent field for a person skilled in the art. The present invention can be carried out based on the contents disclosed in the present specification and common technical knowledge in the pertinent field.

A specific feature of the method for producing a biological organic material that is disclosed herein is that a substantially spherical liquid droplet is cultured in a non-fixed state thereof (typically in a state in which the liquid droplet is repelled by the water-repellent surface and can be moved thereon, while maintaining a substantially spherical shape) on the water-repellent surface formed on a substrate from a material suitable for culturing the desired biological organic material (for example, a culture vessel made from a typical synthetic resin), and the composition of the liquid droplet or the type of the biological organic material that is the production object are not specifically limited.

As described hereinabove, because the method disclosed herein can be a culturing method (three-dimensional culturing method) advantageously suitable for inducting stem cell differentiation, a variety of stem cells are suitable as advantageous biological organic materials. The preferred examples include embryonic stem cells (ES cells), EG stem cells, somatic stem cells, for example, mesenchymal stem cells, hematopoietic stem cells, hepatic stem cells, neural stem cells, marrow stem cells, and corneal epithelial stem cells derived from humans and other mammals (mice, rats, dogs, cats, rabbits, and other domestic animals). Cells other than stem cells can be also cultured and produced in a desired state by the method in accordance with the present invention. The preferred examples include skeletal forming cells (cartilage cells, osteoblastic cells), myotube cells, and fat cells that can be differentiated from mesenchymal stem cells.

Further, a variety of tissues (or cell masses) that were directly sampled from a test body or differentiated from an appropriate stem cell can be advantageously cultured and produced by the method in accordance with the present invention. The preferred examples of suitable tissues include cartilage tissue, bone tissue, sinew tissue, periodontal tissue, corneal tissue, blood vessel tissue or cell masses that can become the tissues.

The liquid droplet (water droplet) that can be used to carry out the present invention can be water, buffer solution, and a variety of culture media for culturing biological organic materials. No specific limitation is placed on the composition of the liquid droplet that will be used, provided that it has been conventionally used for cell or tissue culturing. A culture with a composition suitable for the biological organic material that is the object of culturing (production) can be appropriately selected and used. Further, a variety of additives can be added to the solution for forming the liquid droplet, provided that the additives do not affect the production of biological organic material. For example, various nutrients (inorganic component such as vitamins, organic components such as blood serum), differentiation inducers, pH adjusting agents, preservatives, viscosity controlling agents, antioxidants, perfumes, and colorant can be added.

The size (volume) of liquid droplets can differ depending on the properties of the biological organic material that will be cultured therein, physical properties of the solution constituting the liquid droplet, form of the substrate (culture vessel) having a water-repellent surface, and water repellency of the water-repellent surface. A volume of 100 μL or more is suitable, and 200 μL or more (for example, 200 μL to 1000 μL) is preferred. Where a biological organic material is cultured in a liquid droplet with a volume of 500 μL or more (for example 500 μL to 1000 μL), the production efficiency can be increased.

The culture vessel for use in the method for producing a biological organic material that is disclosed herein is a vessel (for example, a Petri dish or a microtiter plate) that is characterized by having an appropriate substrate (vessel body) and a water-repellent surface formed in part (typically a liquid droplet disposition portion surrounded by circumferential walls or partition portions) of the substrate surface, and a location where the culture medium, that is, a liquid droplet is to be placed is formed on the water-repellent surface. The material, size, and shape of the substrate (vessel body) can differ according to the object.

A variety of the conventional well-known substrates that have been used for culturing cells can be employed without any limitation as the substrate (vessel body) for manufacturing the vessel. Examples of materials for the substrate include glass, silicon, ceramics, metals, and polymer materials. A typical silica glass substrate can be used advantageously. Substrates from ceramics such as silica, alumina, and apatite also can be used advantageously. Metals such as gold, silver, and copper are also examples of materials suitable for the substrate. Examples of preferred polymer materials include polyacetals, polyamides, polycarbonates, ABS resins, polyimides, fluorine resins, polyethylenes, polypropylenes, polystyrenes, and derivatives thereof. In addition to substrates for these polymer materials (synthetic resins), a cotton fibroin film substrate may be also used. The water-repellent surface is formed on at least part (typically the entire location that can be the upper surface of the substrate where the liquid droplet will be located, or part thereof) of the substrate (vessel body) composed of the aforementioned suitable materials.

No specific limitation is placed on a method for forming a water-repellent surface on the substrate, and the substrate surface can be subjected to water repellent treatment by using a water-repellent agent (for example, an agent for forming a fluorine resin coating) that does not inhibit the production of a biological organic material. A suitable contact angle (contact angle with water) is 120° or greater, preferably 130° or greater, and more preferably 140° or greater. It is especially preferred that a super-repellent surface with a contact angle (contact angle with water) of 150° or greater (for example, 150° to 160°) be formed. With the water-repellent surface on which such a high contact angle can be realized, a liquid droplet (water droplet) of a comparatively high volume composed of a usual culture can maintain a substantially spherical shape (typically a perfectly spherical shape). Further, the contact angle can be measured by a variety of well-known conventional methods. For example, a static contact angle (for example, with a liquid droplet diameter of about 2 mm) with distilled water can be measured by using a contact angle meter (for example, CA-X150 model manufactured by Kyowa Interface Science Co., Ltd.) in an atmosphere at 25° C. by a liquid droplet method.

FIG. 1 is a photograph showing the state (spherical) of a liquid droplet obtained when different volumes of water were dropped on a water-repellent surface on which the static contact angle (for example, with a liquid droplet diameter of about 2 mm) with distilled water that is measured by the aforementioned method is 150° or greater. As clearly shown in the figure (photo), a liquid droplet with a volume of 10 μL to 30 μL has a substantially true spherical shape on such water-repellent surface. Further, on the water-repellent surface of such level (the static contact angle is 150° or greater), even liquid droplets of a relatively large volume such as 100 μL to 200 μL can maintain a substantially spherical shape. Thus, liquid droplets of all the volumes shown in FIG. 1 are typical examples included in the "substantially spherical liquid droplet" of the present specification.

It is preferred that a water-repellent layer comprising a compound having a hydrophobic moiety be formed on the substrate surface. As a result, a water-repellent surface demonstrating advantageous water repellency over a long period can be introduced into the substrate. A monomolecular layer composed of such compound is especially preferred.

The water-repellent layer can be formed from a variety of well-known conventional high-molecular compounds having a hydrophobic moiety (typically a hydrophobic group). For example, high-molecular substances having a functional group that can be bonded to the substrate and a substituted or non-substituted alkyl group, alkenyl group, or alkynyl group (the number of carbon atoms is 1 or more, preferably 5 or more; for example, a relatively long carbon chain with 10 to 30 carbon atoms) can be used advantageously.

Such a compound having an alkyl (or alkenyl or alkynyl) chain can easily form a monomolecular layer (that is, a self-assembled monolayer) with a high density and a high degree of orientation by van der Waals force between the chains when the compound is bonded to the substrate surface. Further, due to the presence of alkyl groups, which are hydrophobic moieties (for example, the number of carbon atoms is 1 to 30), high water repellency can be demonstrated.

For example, when the substrate is made from silicon having silanol groups on the surface thereof (culture bed), an organosilicon compound having a relatively long main chain or side chain and having a functional group (preferably, a group that can be bonded to a reactive group present on the culture bed surface) that can be bonded to the culture bed, such as a methoxy group, is preferred as a compound for forming the water-repellent layer. A preferred example of such compound is alkyltrialkoxysilane represented by a general formula $C_nH_{2n+1}Si(OC_mH_{2m+1})_3$ (preferably n is a natural number selected from 10 to 30; m is 1 or 2).

Examples of other preferred compounds include organic compounds having a functional group that can be bonded to the substrate and a partially or entirely fluorine-substituted alkyl group, alkenyl group, or alkynyl group. A compound having a relatively long alkyl (or alkenyl or alkynyl) group is especially preferred because it can easily form a monomolecular layer. No specific limitation is placed on fluorine substitution ratio, but a compound in which more than half (for example, 70% or more hydrogen atoms) hydrogen atoms constituting the alkyl chain or essentially all hydrogen atoms are substituted with fluorine atoms is preferred. For example, an alkyltrialkoxysilane represented by the general formula above in which 70% or more hydrogen atoms constituting the alkyl chain are substituted with fluorine is preferred.

Any conventional well known method can be applied without limitation as a method for forming the water-repellent layer comprising the aforementioned compound on the substrate surface (liquid droplet disposition portion).

Typically, the substrate surface is first subjected to activation treatment such as chemical treatment, plasma treatment, and UV irradiation treatment in order to introduce to the substrate surface a variety of reactive groups (surface functional groups) for chemically bonding the target compound to the substrate surface. For example, when the substrate is from silicon or the like, the substrate surface is hydrophilized (more specifically, silanol groups, that is, hydroxyl groups are introduced), for example, by irradiating the substrate with vacuum UV radiation in air or under reduced pressure. When irradiation is performed in an atmosphere containing oxygen, organic components remaining on the substrate surface can be removed by ozone generated from the atmospheric oxygen by such UV irradiation. The activated substrate is then treated in the vapor phase of the organic compound, the organic compound is grown on the substrate, and a water-repellent layer can be formed.

Figure 2:
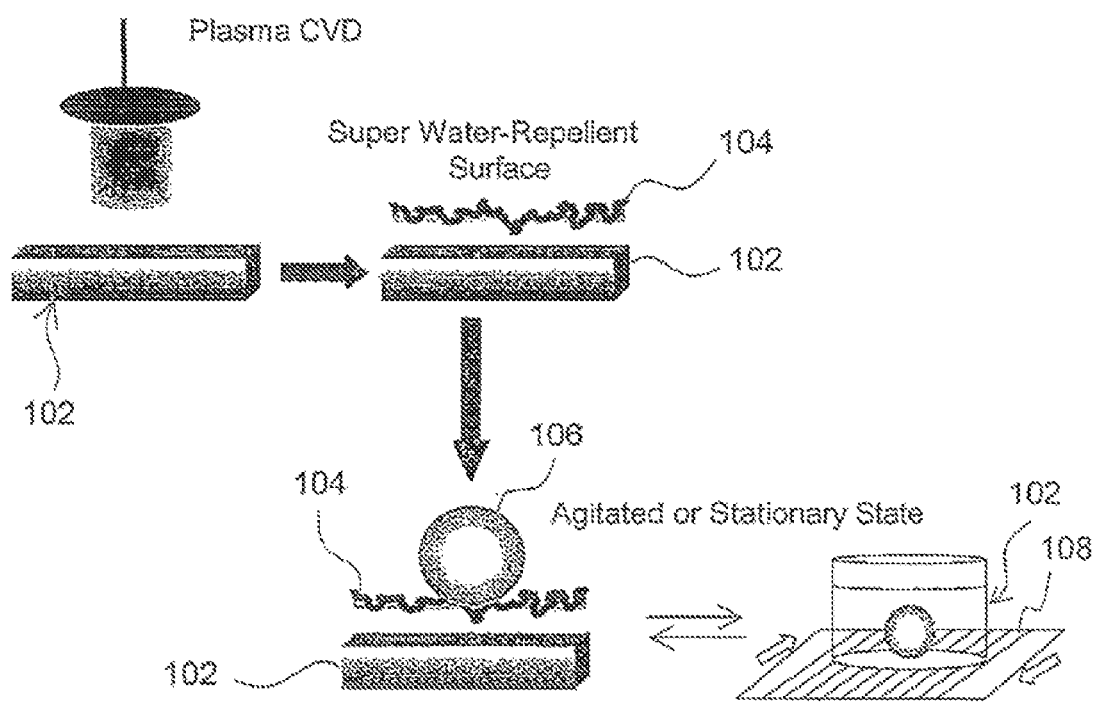
FIG. 2 is a schematic drawing illustrating the fabrication of a culture vessel (substrate) for use in the method for producing a biological organic material in accordance with the present invention and a mode of using the culture vessel.

Alternatively, as shown schematically in FIG. 2, a plasma CVD method may be employed in which the starting material gas comprising an organic compound is excited to a plasma state and then a thin film is formed by a chemical reaction in a gas phase on the substrate surface by using this active plasma. With this method, a water-repellent surface (super-repellent layer) 104 can be formed on the surface of a substrate 102 at a temperature close to room temperature. Therefore, for example, this method is preferred for forming the water-repellent layer 104 on the substrate 102 (for example, a Petri dish made from polystyrene or multiwell plate) made form a high-molecular material (synthetic resin) with a low heat resistance.

It is preferred that a monomolecular layer in which an organic compound is oriented in the predetermined direction be formed as a water-repellent layer. By forming a monomolecular layer, it is possible to obtain a constant layer thickness and impart uniform water repellency to the surface. When a water-repellent layer is grown from a monomolecular layer, the monomolecular layer can be formed by removing the excessively adsorbed molecules as desired. No specific limitation is placed on a method for forming the monomolecular layer, and acid treatment, alkali treatment, and washing with water can be performed in appropriate combination according to the substances used.

Several preferred embodiments of the culture vessel provided by the present invention will be explained below with reference to the appended drawings.

Figure 3:
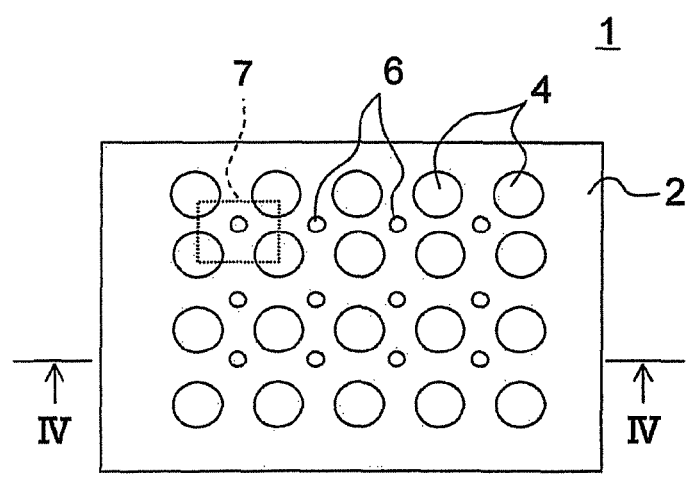
FIG. 3 is a plane view illustrating schematically the outer shape of the culture vessel of one embodiment.
Figure 4:
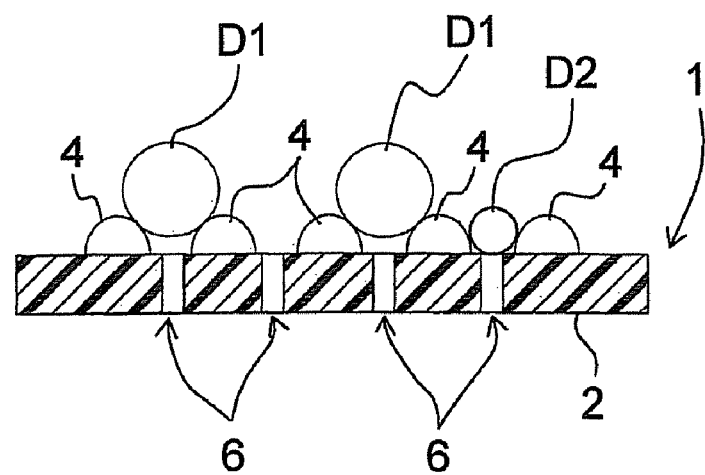
FIG. 4 is a cross-sectional view along the IV-IV line of FIG. 3.

In one preferred embodiment of a portion where a water-repellent surface is formed, a space is formed such that air or other gas can be supplied (that is, caused to be present) in a portion immediately below a liquid droplet. For example, the below-described embodiment in which ventilation holes are provided in parts (liquid droplet disposition portions) of a substrate or an embodiment in which protruding portions equivalent to support stands for supporting spherical liquid droplets are provided with an appropriate spacing on a substrate are preferred. A mesh-like configuration (the fine holes constituting the mesh may have uniform or nonuniform size) composed of a band-like substrate is another preferred form. For example, in an advantageous embodiment, a culture vessel 1 has a form such as shown in FIG. 3 and FIG. 4. In the culture vessel 1, a rectangular plate-like substrate 2 made from a synthetic resin such as polystyrene serves as a container body. A lid that covers the liquid droplet disposition portions (that is, the upper surface of the substrate 2) may be provided (this lid is not shown in the figure).

As shown in FIG. 3 and FIG. 4, a plurality of protruding portions (partition portions) 4 that are arranged as a rectangular grid are formed on the upper surface of the substrate 2. As shown in FIG. 3, the top of the protruding portion 4 is rounded to have a semispherical shape. Water repellency (preferably, contact angle with water of 130° or more, more preferably super-repellency of an angle of 150° or more) is imparted by the below-described treatment to the upper surface of the substrate 2 and the surface of the protruding portions (partition portions) 4. As shown in the figure, a ventilation hole 6 passing through from the upper surface to the lower surface of the rectangular plate-like substrate 2 is formed in the central portion of each portion of the upper surface of the substrate (see portion represented by dot line and denoted by the reference numeral 7 in FIG. 3) that is surrounded by four adjacent protruding portions (partition portions) 4.

Because of the above-described configuration, in the culture vessel 1 of the present embodiment, a portion including a ventilation hole 6 surrounded by four adjacent protruding portions (partition portions) 4 constitutes a liquid droplet disposition portion 7.

Thus, as shown in FIG. 4, when a culture medium of a comparatively small volume is supplied to such liquid droplet disposition portion 7, the culture medium forms a substantially spherical liquid droplet D2 due to water repellency of the substrate surface and maintains a spherical shape in this portion in an non-fixed state. At this time, if the diameter of the liquid droplet D2 is larger than the spacing between two adjacent protruding portions 4, the protruding portions located on the circumference of the liquid droplet disposition portion 7 serve as partition portions and can prevent the liquid droplet (culture medium) from flowing out of the liquid droplet disposition portion 7. This is because the spherical shape of the liquid droplet D2 is maintained and does not change since the entire surface of the substrate 2 in a surrounding zone that can be in contact with the liquid droplet D2 is water repellent.

Thus, in the culture vessel 1 of the present embodiment, liquid droplets D2 of a comparatively small size (a diameter larger than the spacing between two adjacent protruding portions 6 and smaller than a portion surrounded by four adjacent protruding portions (partition portions) 4) can be held with high stability in predetermined positions on the substrate surface. As a result, by providing a large number of such holding locations, it is possible to position and arrange a large number of liquid droplets D2 on the surface of the substrate 2 of one culture vessel 1, without mutual fusion of the droplets. Further, because ventilation holes 6 are provided directly below the liquid droplets D2 disposed in the predetermined liquid droplet disposition portions 7, good gas exchange can be realized even under the liquid droplets D2. Therefore, by using the culture vessel 1 of the present embodiment, it is possible to culture and produce the target biological organic material with good efficiency.

The size of the aperture diameter of the ventilation hole 6 should not be limited specifically as long as the shape of a liquid droplet in a desired size can be maintained and satisfactory gas exchange can be performed from the bottom side that includes a position immediately below the liquid droplet. The average diameter of the ventilation hole is preferably about from 0.1 mm to 2 mm and more preferably about from 0.2 mm to 1 mm.

Further, in the culture vessel 1 of the present embodiment having the above-described configuration, the four adjacent protruding portions 4 serve as a support portion and can hold thereupon a liquid droplet of a comparatively large diameter.

More specifically, a culture medium is supplied so that a semispherical apex portions of the four mutually adjacent protruding portions 4 constituting the outer periphery of the liquid droplet disposition portion 7 shown by a dot line in FIG. 3 become support points. At this time, by appropriately adjusting the amount of supplied culture medium, it is possible to form a liquid droplet D1 of a diameter larger than the distance between two protruding portions 4 located on a diagonal of the rectangular (see dot line shown by the reference numeral 7 in FIG. 3) configured by the four protruding portions 4.

Further, because the liquid droplet D1 of this size cannot penetrate into a portion (the aforementioned liquid droplet disposition portion 7) surrounded by the four protruding portions 4 and also because the entire surface of the substrate 2 (the surfaces of the protruding portions) in a surrounding zone that can be in contact with the liquid droplet D1 is water repellent, the liquid droplet is held on the semispherical apex portions of the four mutually adjacent protruding portions 4, as shown in FIG. 3, while maintaining its substantially spherical shape.

Thus, in the culture vessel 1 of the present embodiment, liquid droplets D2 of a comparatively large size (a diameter larger than the distance between two protruding portions 4 located on a diagonal of the rectangular configured by the four adjacent protruding portions 4) can be disposed with good stability on the protruding portions 4. As a result, by providing a large number of such protruding portions 4 (disposition locations), it is possible to position and arrange a large number of liquid droplets D1 on the substrate 2 of one culture vessel 1, without mutual fusion of the droplets. Further, when the liquid droplets D1 are disposed in this state, portions immediately below the liquid droplets are located above the substrate 2 (see FIG. 4) and, therefore, good gas exchange can be realized even under the liquid droplets D1.

Therefore, by using the culture vessel 1 of the present embodiment, it is possible to culture and produce the target biological organic material with good efficiency.

From the standpoint of production efficiency of biological organic materials, it is preferred that the arrangement spacing of the aforementioned protruding portions (that is, the distance between two adjacent protruding portions) be so determined that the liquid droplets of a volume of about 50 μL or more, preferably 100 μL or more be disposed on the protruding portions, but this size of the liquid droplets is not limiting. For example, the distance between two adjacent protruding portions is preferably about 0.1 mm to 2 mm, more preferably 0.2 mm to 1 mm.

Further, the arrangement of protruding portions 4 on the surface of the surface 2 is not limited to the above-described rectangular grid-like arrangement. For example, the same effect can be obtained with the arrangement of a culture vessel 10 shown in FIG. 5 that is a modification example of the above-described embodiment.

Figure 5:
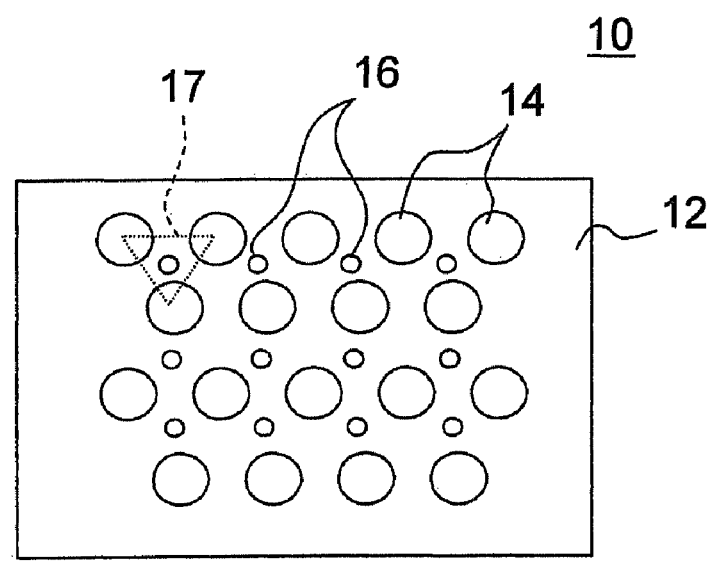
FIG. 5 is a plane view illustrating schematically the outer shape of the culture vessel of another embodiment.

Thus, in the culture vessel 10 shown in FIG. 5, a plurality of protruding portions (partition portions) 14 are formed as an oblique (rhomboidal) grid on the upper surface of a rectangular plate-like substrate 12. As shown in the figure, a ventilation hole 16 is formed in the center of a portion (portion bounded by a dot line represented by the reference numeral 17 in FIG. 5) of the upper surface of the substrate surrounded by three adjacent protruding portions (partition portions) 14. In the culture vessel 10 of such form, a portion including a ventilation hole 6 surrounded by three adjacent protruding portions (partition portions) 14 constitutes a liquid droplet disposition portion 17. Therefore, similarly to the above-described embodiment shown in FIG. 3 and FIG. 4, when a culture medium of a comparatively small volume is supplied to the liquid droplet disposition portion 17, the culture medium forms a substantially spherical liquid droplet (not shown in the figure) due to water repellency of the substrate surface and maintains a spherical shape in this portion in a non-fixed state. At this time, if the diameter of the liquid droplet is larger than the spacing between two adjacent protruding portions 14, the protruding portions 14 located on the circumference of the liquid droplet disposition portion 17 serve as partition portions and can prevent the liquid droplet (culture medium) from flowing out of the liquid droplet disposition portion 17.

On the other hand, in the culture vessel 10 of the present embodiment, a liquid droplet of a comparatively large diameter can be held on three adjacent protruding portions 14 as a support portion. Thus, by appropriately adjusting the amount of supplied culture medium, it is possible to form a liquid droplet (not shown in the figure) of a diameter larger than the distance between two adjacent protruding portions 14 of the triangle configured by the three mutually adjacent protruding portions 14 constituting the outer periphery of the liquid droplet disposition portion 17 shown by a dot line in FIG. 5. Where the liquid droplet of this size cannot penetrate into a portion (the aforementioned liquid droplet disposition portion 17) surrounded by the three protruding portions 14 and where the entire surface of the substrate 12 (that is, the surface of protruding portions 14) in a surrounding zone that can be in contact with the liquid droplet is water repellent, the liquid droplet is held on the semispherical apex portions of the three mutually adjacent protruding portions 14.

The preferred embodiment of the culture vessel in accordance with the present invention is not limited to that having protruding portions such as shown in the above-described FIG. 3 to FIG. 5.

Figure 6:
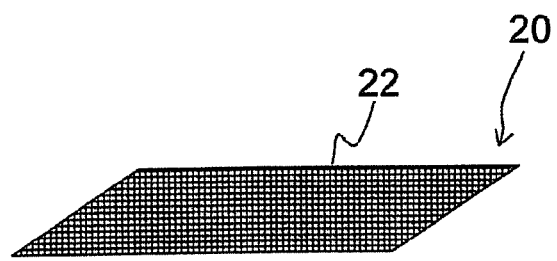
FIG. 6 is a perspective view illustrating schematically the outer shape of the culture vessel of another embodiment.

For example, a culture vessel 20 comprising a mesh-like substrate 22 typically made from a metal or a resin, such as shown in FIG. 6, may be also used. By providing the surface of the mesh-like substrate 22 with water repellency that is preferred for carrying out the present invention, substantially spherical liquid droplets of a desired size can be formed on the mesh. Further, because a lower portion (lowermost portion) of the liquid droplet is disposed in a clearance (pore) portion of the mesh-like substrate 22, good gas exchange can be realized from the lower surface side of the liquid droplet including the zone immediately therebelow. The opening diameter (that is, a mesh size) of the gap (pore) portion of the mesh-like substrate 22 is preferably about 0.1 mm to 2 mm, more preferably about 0.2 mm to 1 mm.

Portions for disposing the liquid droplets are not limited to a mesh-like configuration, and it is not necessary that the entire such substrate be configured of the mesh portion. Thus, meshes may be provided only in part of the substrate (vessel body).

Figure 7:
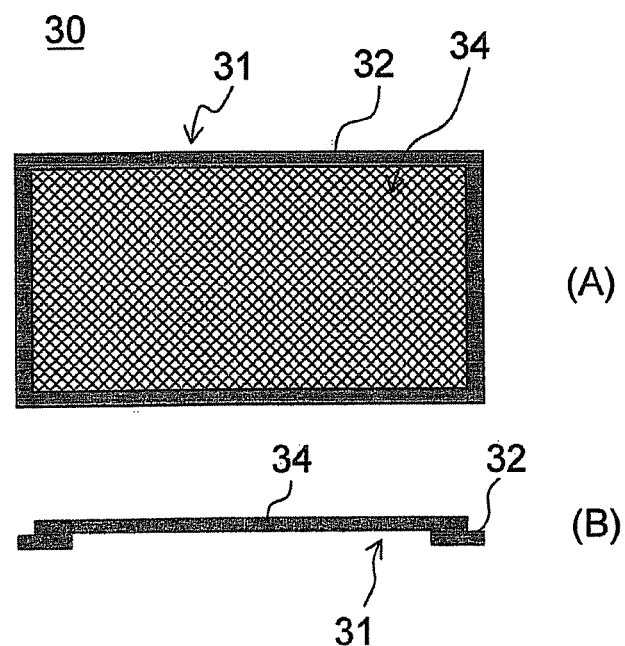
FIG. 7 illustrates schematically the outer shape of the culture vessel of another embodiment.

For example, a culture vessel 30 having a substrate 31 comprising a mesh portion 34 for arranging liquid droplets and a support stand 32 disposed in the circumferential edge portion on the back surface side of the mesh portion 34, as shown in FIGS. 7(A), (B), is also a culture vessel of a preferred embodiment provided by the present invention. With such embodiment, mechanical strength of the mesh portion 34 can be increased and good gas supply can be ensured from the back side (disposition side of the support stand 32) of the mesh portion 34 to the lower surface of liquid droplets disposed on the surface (upper surface) of the mesh portion 34.

The mesh surface is not limited to a flat shape, such as shown in the figure. For example, the surface may be subjected to emboss (peak-valley) processing. Where peaks and valleys are present on the mesh surface, liquid droplets can be arranged in the concave portions. As a result, positioning of liquid droplets and holding in the predetermined positions are facilitated.

Figure 8:
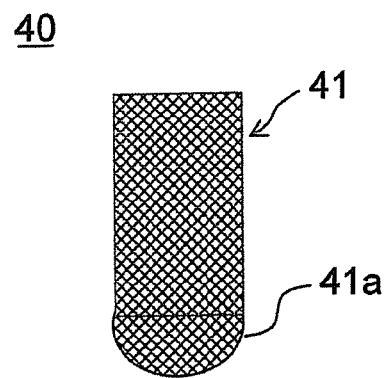
FIG. 8 is a side view illustrating schematically the outer shape of the culture vessel of another embodiment.

Alternatively, a culture vessel 40 that is a substrate 41 in the form of a well-known typical culture tube, such as shown in FIG. 8, in which at least a bottom portion 41a for arranging liquid droplets that is a mesh portion having the desired water repellency (in the configuration shown in the figure, the entire tubular substrate 41 is configured of mesh portions) is also a culture vessel (culture tube) of a preferred embodiment provided by the present invention. The culture vessel of such embodiment is easy to handle (in particular, carry), and by preparing a large number of tubular culture vessels 40 of the same shape, it is possible to culture and produce a large quantity of liquid droplets of the same shape under the same conditions in a limited space.

The present invention was explained above with reference to specific embodiments, and in the culture vessel provided by the present invention liquid droplets of a substantially spherical shape are easily formed by dropping a predetermined culture medium on a water-repellent (super-repellent) surface of a vessel body (substrate). Because the liquid droplets have a substantially spherical shape (typically, a spherical shape such as in FIG. 1), a target biological organic material (for example, stem cells) can be three-dimensionally cultured in the liquid droplets. Therefore, stem cells can be differentiated to a desired tissue (cell mass) in the liquid droplets. For example, a biological organic material that is cultured with differentiation from appropriate stem cells (for example, mesenchymal stem cells) to cartilage tissue can be produced.

Therefore, with the method for producing a biological organic material that is disclosed herein, as shown schematically in the above-described FIG. 2, a predetermined culture medium is dropped on a water-repellent surface 104 of a culture vessel (substrate) 102, almost spherical liquid droplets 106 are formed, and a target biological organic material (for example, stem cells) are cultured in the liquid droplets 106. Further, with the method in accordance with the present invention, because the liquid droplets 6 have a substantially spherical shape (preferably, a perfectly spherical shape as shown in FIG. 1), a good three-dimensional culture space can be provided. Therefore, the stem cells can be differentiated to a desired tissue (cell mass) in the liquid droplets 6. In a preferred example of the disclosed method, the method for producing a biological organic material is accompanied by differentiation from appropriate stem cells (for example, mesenchymal stem cells) to cartilage tissue.

No specific limitation is placed on culturing conditions, and they can be appropriately selected according to the state of the biological organic material (cells). For example, in the case of cells for tissue of mammals, including humans, stationary culturing can be performed at a temperature within a range from room temperature to about the body temperature (that is, 20° C. to 40° C., preferably 33° C. to 38° C.) of mammals. Alternatively, it is possible to dispose the culture vessel (substrate) 102 in an appropriate agitator 108, apply appropriate agitation (reciprocating agitation, rotational agitation, etc.), and perform culturing while causing a flow of a culturing solution or culturing substance constituting liquid droplets in a continuous or intermittent manner. Further, in order to prevent the pH of the culture medium from rising, it is preferred that culturing be performed in a $CO_2$ incubator in which the $CO_2$ concentration in the culture atmosphere is maintained at an almost constant level (for example, 3 to 10%, in particular about 5%).

The present invention will be explained below in greater details by examples thereof, but the present invention should not be construed as being limited to these examples.

Example 1

A water-repellent layer (water-repellent film) was formed on the surface of a commercial tissue culture Petri dish (diameter 3.5 cm, made from polystyrene (PS)) by a typical plasma CVD method. Trimethylmethoxysilane (TMMOS) was used as a starting material for forming the water-repellent layer. Further, argon (Ar) was used as a plasma forming gas. Thus, the PS dish was disposed inside a chamber of a capacitively coupled high-frequency plasma apparatus. The TMMOS gas and Ar gas were introduced into the chamber so as to obtain a pressure of 50 Pa for the former and 30 Pa (a total of 80 Pa) for the latter, and microwave plasma was induced for 5 min at a microwave output of 300 W. The temperature of the PS surface of the Petri dish in this process was 50° C. or less.

Figure 9:
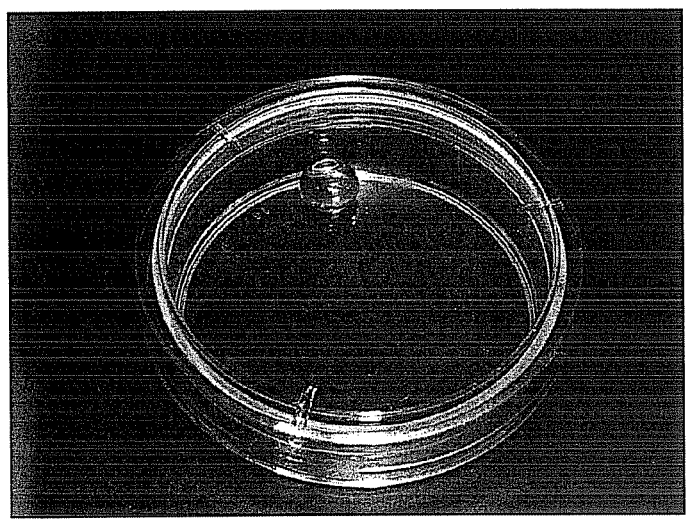
FIG. 9 is a photo illustrating the outer shape of the culture vessel (Petri dish) of one example and a mode of using the culture vessel (state in which a liquid droplet is disposed on a water-repellent surface).

By the above-described treatment, a water-repellent layer having methyl groups, which are hydrophobic groups, on the surface was formed at the inner surface of the circumferential wall of the Petri dish made from PS. As shown in FIG. 9, a water droplet dropped on such water-repellent surface assumed an almost spherical shape. When a contact angle with water was measured by a usually employed method, it was found to be 150° or greater. The Petri dish having the water-repellent surface was then irradiated for 30 min with ultraviolet radiation and sterilized.

Human mesenchymal stem cells were cultured in the below-described manner on the water-repellent surface of the Petri dish thus obtained. Thus, 500 μL of MSCGM culture containing about 2.5×10$^5$ mesenchymal stem cells (culture for human mesenchymal stem cells: product of Sanko Junyaku Co., Ltd.) was dropped on a water-repellent surface of the Petri dish subjected to sterilization and almost spherical liquid droplets were obtained. The dish was then placed into a commercial agitating incubator, and culturing was preformed over 5 days at a temperature of 37° C. in a 5% $CO_2$ atmosphere, while performing reciprocating agitation at a frequency of 60 to 70 cycles/min.

Figure 10:
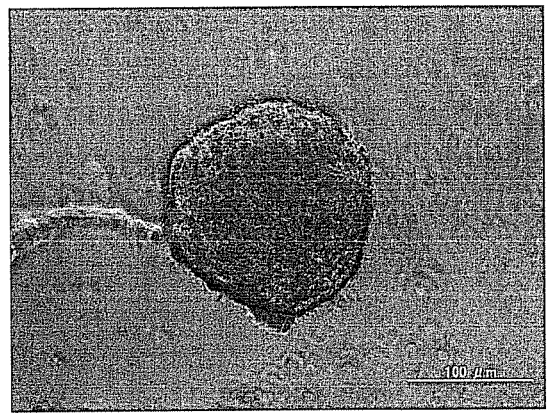
FIG. 10 is a microphotograph illustrating a cell mass (cluster) composed of human mesenchymal stem cells cultured by the method of one example of the present invention.

As a result a cell mass (cluster) composed of mesenchymal stem cells was formed in the liquid droplets, as shown in FIG. 10. The results of Trypan blue staining confirmed the viability of the cells constituting the cell mass. A cell mass of a similar size was also formed in the case where liquid droplets of 250 μL (that is, with two-fold cell concentration) MSCGM culture medium containing about 2.5×10$^5$ mesenchymal stem cells was similarly cultured.

Example 2

Human mesenchymal stem cells were agitated and cultured on a water-repellent surface of a Petri dish similar to that fabricated in Example 1. Thus, 500 μL of control culture medium for cartilage tissue differentiation containing about 2.5×10$^5$ mesenchymal stem cells (culture medium for mesenchymal stem cells: product of Sanko Junyaku Co., Ltd.) was dropped on a water-repellent surface of the pre-sterilized Petri dish and almost spherical liquid droplets were obtained. The dish was then placed into a commercial agitating incubator, and culturing was preformed over 5 days at a temperature of 37° C. in a 5% $CO_2$ atmosphere, while performing reciprocating agitation at a frequency of 60-70 cycles/min.

Figure 11:
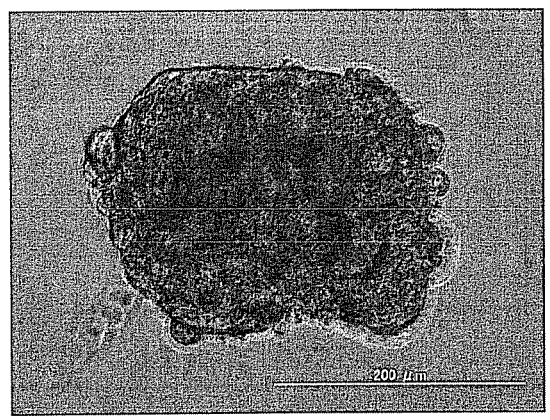
FIG. 11 is a microphotograph illustrating a cell mass (cluster) composed of cartilage cells differentiated from human mesenchymal stem cells cultured by the method of one example of the present invention.
Figure 12:
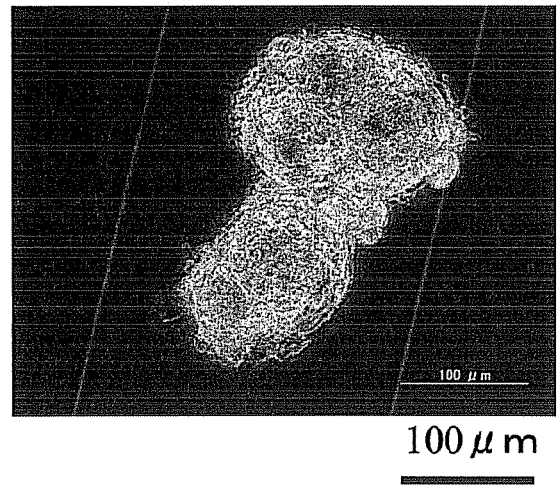
FIG. 12 is a microphotograph illustrating a state after Trypan blue staining of a cell mass (cluster) composed of cartilage cells differentiated from human mesenchymal stem cells cultured by the method of one example of the present invention.

As a result, a cell mass (cluster) composed of cartilage cells differentiated from mesenchymal stem cells was formed in the liquid droplets, as shown in FIG. 11. The results of Trypan blue staining confirmed the viability of the cells constituting the cell mass (FIG. 12).

Example 3

Human mesenchymal stem cells were stationary cultured on a water-repellent surface of a Petri dish similar to that fabricated in Example 1. Thus, 250 μL of control culture for cartilage tissue differentiation containing about 2.5×10$^5$ mesenchymal stem cells (culture for mesenchymal stem cells: product of Sanko Junyaku Co., Ltd.) was dropped on a water-repellent surface of the Petri dish subjected to sterilization and almost spherical liquid droplets were obtained. The dish was then cultured for 10 days at a temperature of 37° C. in a 5% $CO_2$ atmosphere.

Figure 13:
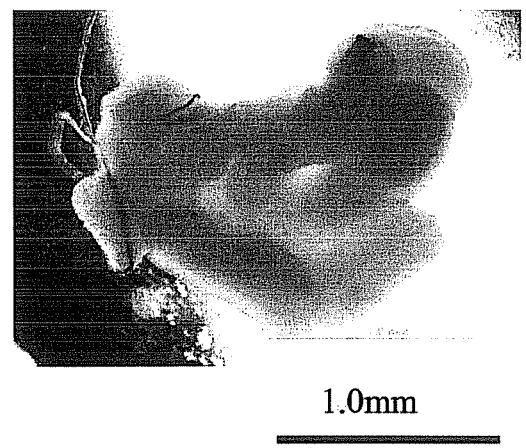
FIG. 13 is a microphotograph illustrating a cartilage formation (cartilage tissue) differentiated from human mesenchymal stem cells cultured by the method of one example of the present invention.

As a result, as shown in FIG. 13, a cartilage formation (cartilage tissue) differentiated from mesenchymal stem cells and further grown from a cell mass was formed in the liquid droplets. The largest cartilage formation was found to have a size of about 1.5 mm.

Comparative Example 1

A commercial Petri dish was used as is, that is, without forming the above-described water-repellent layer (water-repellent film), and culturing of human mesenchymal stem cells was performed under conditions identical to those of Example 1.

Figure 14:
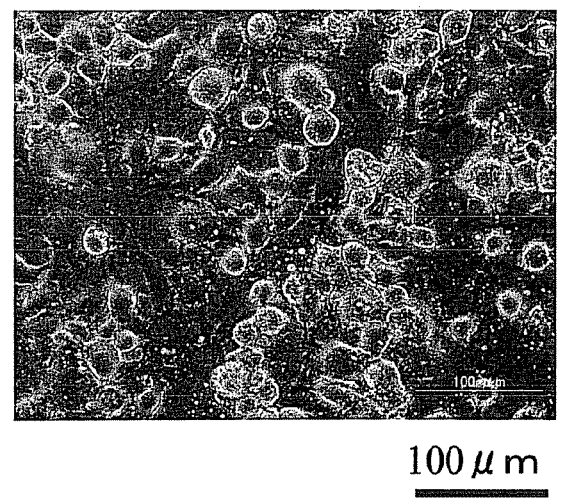
FIG. 14 is a microphotograph illustrating human mesenchymal stem cells cultured in a culture vessel (commercial Petri dish product) having no water-repellent surface.

As a result, as shown in FIG. 14, the mesenchymal stem cells adhered to the Petri dish surface, and no cell mass observed in the above-described examples was present in the culture medium.

Embodiment 4

Figure 15:
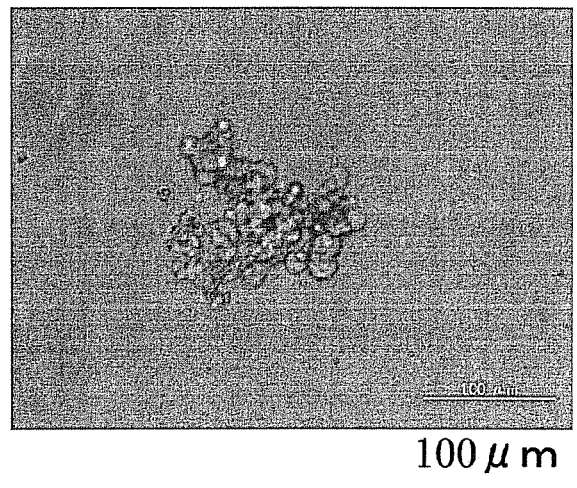
FIG. 15 is a microphotograph illustrating the state after the first day of culturing where mouse ES cells were cultured by the method of one example of the present invention.
Figure 16:
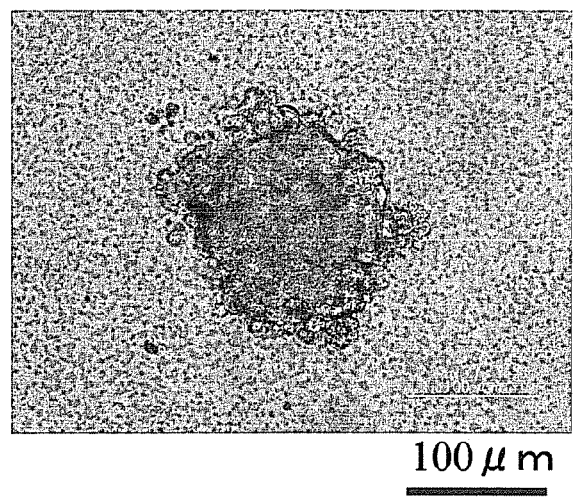
FIG. 16 is a microphotograph illustrating the state after the second day of culturing where mouse ES cells were cultured by the method of one example of the present invention.
Figure 17:
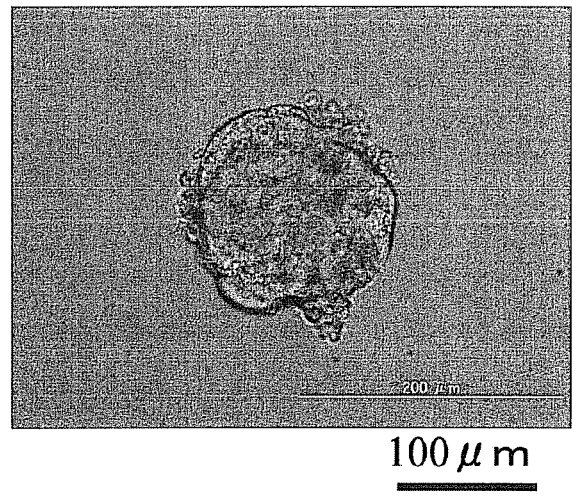
FIG. 17 is a microphotograph illustrating the state after the third day of culturing where mouse ES cells were cultured by the method of one example of the present invention.
Figure 18:
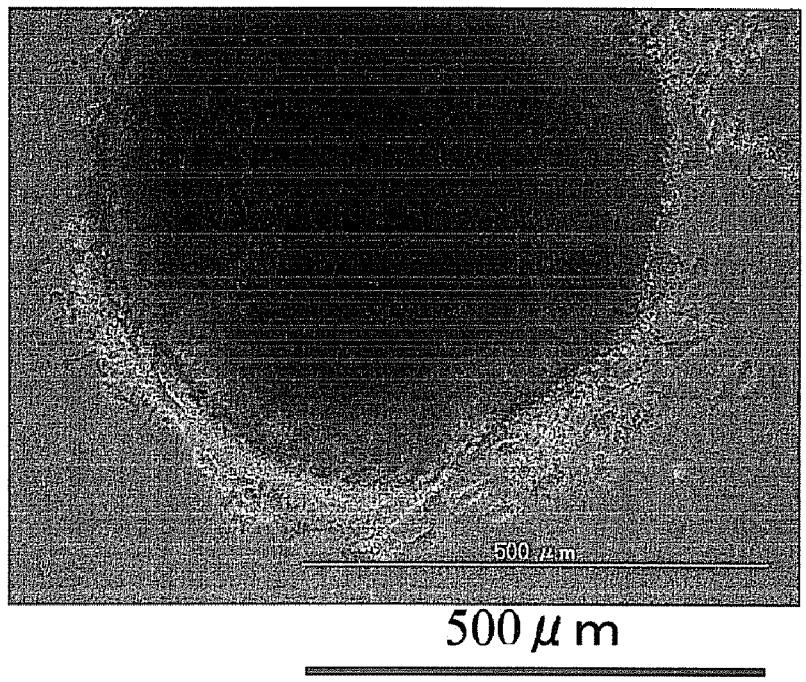
FIG. 18 is a microphotograph illustrating the state after the seventh day of culturing where mouse ES cells were cultured by the method of one example of the present invention.

Mouse ES cells were stationary cultured on a water-repellent surface of a Petri dish identical to that fabricated in Examples 1. Thus, 500 μL of commercial culture medium for ES cells containing about 1×10$^3$ to 10$^4$ mouse ES cells (product of Dainippon Pharmaceutical Co., Ltd.) was dropped on a water-repellent surface of the pre-sterilized Petri dish and almost spherical liquid droplets were obtained. The dish was then cultured at a temperature of 37° C. in a 5% $CO_2$ atmosphere. As a result, as shown in FIGS. from 15 to 18, cohesion of ES cells that aggregated in the first day of culturing was observed (FIG. 15). In the second and third days of culturing, a cell mass (cluster) of a diameter of 100 μm to 150 μm was formed (FIG. 16, FIG. 17). In the seventh day of culturing, the cell mass diameter has grown to about 500 μm (FIG. 18).

Example 5

A commercial 96 multiwell plate (U-bottom 96-well microtiter plate) made from polystyrene was used as a substrate of a culture vessel. Protruding portions with semi-spherical top portions corresponding to U bottoms of 96 wells were arranged regularly in the form of a square grid on the rear surface (lower surface) of the multiwell plate (see FIG. 3 and FIG. 19). A water-repellent layer (water-repellent film) was formed by a general plasma CVD method on the rear surface having peaks and valleys (abbreviated hereinbelow as "peak-valley surface"). Trimethylmethoxysilane (TMMOS) was used as a starting material for forming the water-repellent layer. Argon (Ar) was used as a plasma forming gas.

Thus, the multiwell plate was disposed inside a chamber of a capacitively coupled high-frequency plasma apparatus. The TMMOS gas and Ar gas were introduced into the chamber so as to obtain a pressure of 50 Pa for the former and 30 Pa for the latter (a total of 80 Pa), and microwave plasma was induced for 5 min at a microwave output of 300 W. The temperature of the peak-valley surface in this process was 50° C. or lower.

Figure 19:
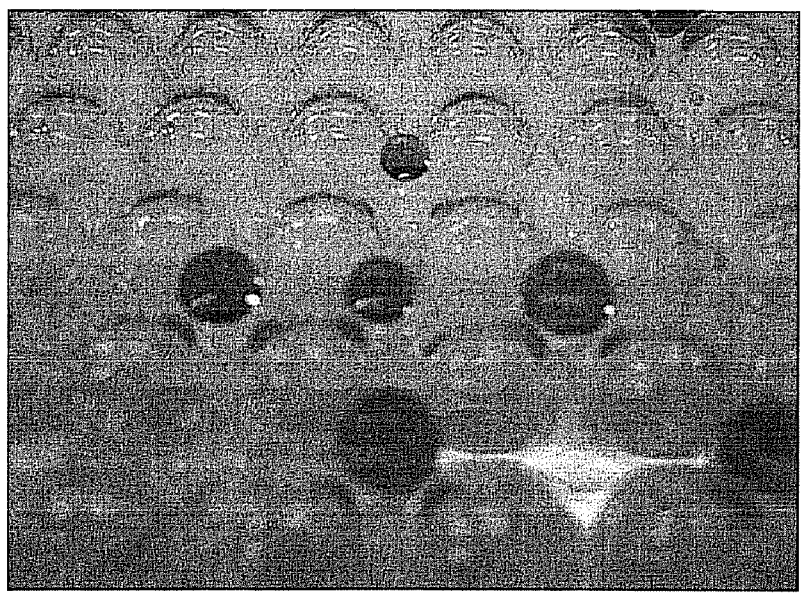
FIG. 19 is a photograph illustrating the state of a liquid droplet disposed in the culture vessel of Example 5.

By the above-described treatment, a water-repellent layer having methyl groups, which are hydrophobic groups, was formed on the peak-valley surface of the multiwell plate made from PS. As shown in FIG. 19, a water droplet (contained a dye such as crystal violet to facilitate recognition) dropped on such water-repellent surface assumed an almost spherical shape. When a contact angle with water was measured by a usually employed method, it was found to be 150° or greater. FIG. 19 clearly shows that a liquid droplet of a comparatively large diameter is disposed on protruding portions in a state of being supported by four adjacent protruding portions. The culture vessel of the present embodiment that had the water-repellent surface was then irradiated for 30 min with ultraviolet radiation and sterilized.

Example 6

Figure 20:
FIG. 20 is a photograph illustrating the state of a liquid droplet disposed in the culture vessel of Example 6.

A commercial tea strainer was used as a substrate of a culture vessel. As shown in FIG. 20, the tea strainer comprised a metallic mesh portion (average size of meshes (gaps):

about 1.5 mm) and a ceramic annular frame holding the circumferential edge of the mesh portion.

A water-repellent layer (water-repellent film) was formed on the metallic mesh portion by the same method as in Example 5. As shown in FIG. 20, a water droplet (contained a colorant) dropped on such water-repellent surface assumed an almost spherical shape. When a contact angle with water was measured by a usually employed method, it was found to be 150° or more.

Example 7

Mouse ES cells were cultured by using the culture vessel of Example 5 that was obtained in the above-described manner.

Figure 21:
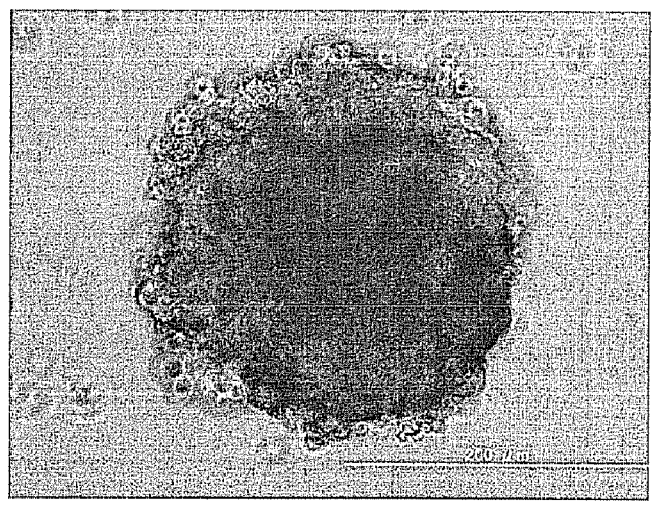
FIG. 21 is a microphotograph illustrating the state after the third day of culturing where mouse ES cells were cultured in the culture vessel (liquid droplet) of Example 5.
Figure 22:
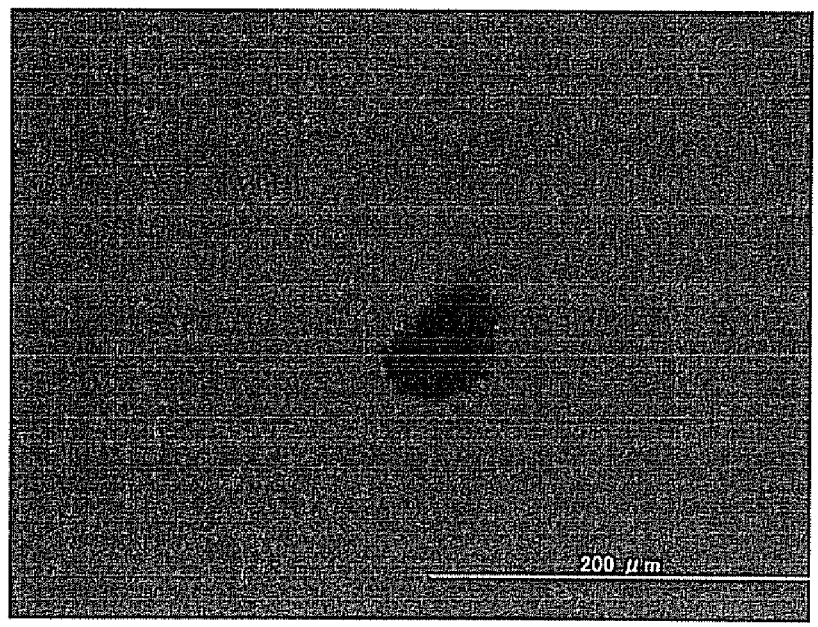
FIG. 22 is a microphotograph illustrating the state after the third day of culturing where mouse ES cells were cultured in wells of a 96-multiwell plate used as a comparative example.

Thus, 150 μL of commercial culture medium for ES cells containing about $10^5$ mouse ES cells (product of Dainippon Pharmaceutical Co., Ltd.) was disposed in the form of liquid droplets on the protruding portions of the culture vessel of Example 5. The plate was then cultured for 3 days at a temperature of 37° C. in a 5% $CO_2$ atmosphere. For comparison, 150 μL of the commercial culture medium for ES cells containing about $10^3$ mouse ES cells was injected into U-bottom wells of a commercial 96-multiwell plate made from polystyrene used in Example 5 and culturing was performed under the same conditions. As a result, as shown in FIG. 21, a large cell mass (cluster) with a diameter of 200 μm or greater that was formed by aggregation of ES cells was formed inside the liquid droplets cultured for 3 days in the culture vessel of Example 5. The results of Trypan blue staining confirmed the viability of the cells constituting the cell mass. On the other hand, as shown in FIG. 22, only a small cell mass with a diameter of 100 μm or less was observed in the medium cultured in the U-bottom wells of the comparative example. The results presented above confirmed that by using the culture vessel in accordance with the present invention, it is possible to produce a biological organic material such as ES cells with good efficiency.

Example 8

A 96-multiwell plate (U-bottom 96-well multititer plate) made from polystyrene that was identical to that used in Example 5 was used as the substrate of the culture vessel. A water-repellent layer (water-repellent film) was formed by a typical plasma CVD method on the rear surface (that is, peak-valley surface) of the multiwell plate.

Thus, the multiwell plate was disposed inside a chamber of a capacitively coupled high-frequency plasma apparatus. In the present embodiment, TMMOS was used as a starting material for forming a water-repellent layer, and Ar was used as a plasma forming gas. In the present embodiment, the gas pressure of TMMOS inside the chamber was set to 30% of the total pressure (TMMOS+Ar). The total pressure was set to 60 Pa, 65 Pa, or 75 Pa.

The gas mixture was introduced into the chamber to obtain such gas pressure (molar ratio of TMMOS and Ar), and microwave plasma was applied over 5 min at a microwave output of 300 W. The temperature of the peak-valley surface of the multiwell plate in this process was 50° C. or lower. By the above-described treatment, a water-repellent layer having methyl groups, which are hydrophobic groups, was formed on the peak-valley surface of the multiwell plate made from PS. The contact angle of the water-repellent surface with water was 150° or greater. The plate (culture vessel) was irradiated for 30 min with UV radiation to sterilize the plate.

Embodiment 9

Mouse ES cells were cultured in the below-described manner by using the culture vessel of Example 8 obtained as described above.

Thus, 20 μL of a commercial culture medium for ES cells (product of Dainippon Pharmaceutical Co., Ltd.) containing about $4\times10^3$ ES cells was disposed in spaces (that is, the position of a liquid drop shown by D2 in FIG. 4) surrounded by four adjacent protruding portions (partition portions) located on the peak-valley surface of the culture vessel obtained in Example 8. For one plate, from six to ten liquid droplets were disposed. Each liquid droplet that was thus disposed had an almost spherical shape and the diameter of the liquid droplet was larger than the width of spacing between the two adjacent protruding portions (partition portions). As a result, the droplets were stably held in this position. The plate was incubated for 3 days at a temperature of 37° C. in a 5% $CO_2$ atmosphere.

Figure 23:
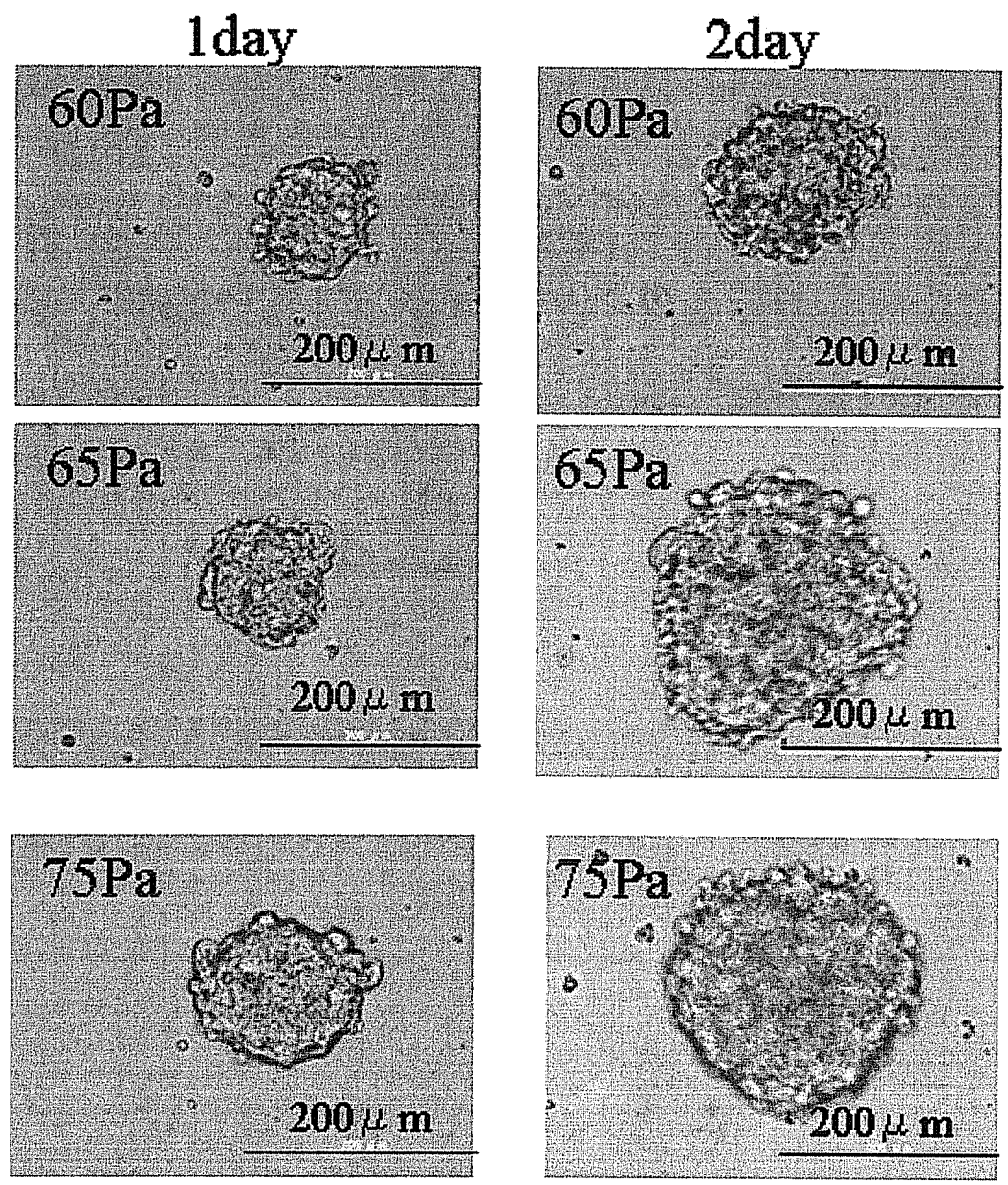
FIG. 23 is a microphotograph illustrating the state after the first and second day of culturing where mouse ES cells were cultured in culture vessels (liquid droplets) of three kinds (different gas pressure conditions during formation of a water-repellent film) of Example 8.

As shown in FIG. 23, in the liquid droplet culturing using the plate with a water-repellent surface fabricated by a plasma CVD method under the aforementioned gas pressure conditions (total pressure inside the chamber 60 Pa, 65 Pa, or 75 Pa), ES cells in the liquid droplets multiplied gradually with the passage of culturing time and large aggregated cell masses (clusters) with a diameter of 100 μm or greater (preferably a diameter of 200 μm or greater) were formed. The results of Trypan blue staining confirmed the existence of cells constituting the cell mass. On day three of culturing, the cell masses were transferred to a dish that was coated with gelatin in advance, and differentiation culturing was performed in an appropriate culture medium. All the cell masses grown to embryoids (EB) that were observed to pulsate.

Example 10

A 96 multiwell plate (U-bottom 96-well multititer plate) made from polystyrene that was identical to that used in Example 5 was employed as a substrate of a culture vessel. A water-repellent layer (water-repellent film) was formed by a general plasma CVD method on the rear surface (that is, on the peak-valley surface) of the multiwell plate. In the present example, the effect of gas pressure on the formation of water-repellent film was studied.

Thus, water-repellent layers (water-repellent films) were formed on the rear surface (that is, on the peak-valley surface) of the plate by the same plasma CVD method as described above with respect to cases in which the gas pressure of TMMOS inside the chamber was set to 30% of the total pressure (TMMOS+Ar) and the total pressure was set to (1) 95 Pa, (2) 75 Pa, and (3) 65 Pa and with respect to a case (4) in which the total pressure was set to 75 Pa and the Ar pressure was set to 30% of the total pressure (therefore, the gas pressure of TMMOS took 70%). Upon formation of the water-repellent film, thickness and surface roughness (central line average roughness Ra and root mean square roughness Rrms) of the water-repellent film were measured using commercial devices. The results are shown in Table 1. As follows from the results (Table 1) of the present example, the present invention can provide a water-repellent film (that is, super-repellent surface) suitable for in-droplet culturing of biological organic materials, such that has a surface roughness (for example Ra) of 50 nm or greater (for example, 50 to 70 nm) and a thickness of 200 nm or greater (for example, 200 to 300 nm).

TABLE 1

| Sample No. | $P_{TMMOS}/P_{ALL}$ | Thickness (nm) | Ra (nm) | Rrms (nm) |
|---|---|---|---|---|
| (1) | 29/95 (Pa) | 267 | 67.33 | 87.7 |
| (2) | 23/75 (Pa) | 204 | 54.15 | 68.89 |
| (3) | 20/65 (Pa) | 191 | 40.48 | 50.23 |
| (4) | 53/75 (Pa) | 179 | 48.2 | 61.6 |

Specific examples of the present invention are described in detail above, but they are merely illustrative examples and place no limitation on the claims. The technology described in the claims includes various modifications and changes of the specific examples described above.

INDUSTRIAL APPLICABILITY

As described above, the method and culture vessel for producing a biological organic material provided by the present invention can be advantageously used for culturing cells (in particular, ES cells and other stem cells) and cell masses (including aggregated embryoids) in a state in which a function of differentiating (aggregating) into the target tissue or organs is maintained. Therefore, the method and culture vessel for producing a biological organic material provided by the present invention have a high utility value in medical industry.

What is claimed is:

1. A method for producing a biological organic material in a liquid droplet comprising a culture medium containing predetermined components, the method comprising:
    disposing a substantially spherical liquid droplet in a non-fixed state on a substrate having a water-repellent surface; and
    culturing the biological organic material in said liquid droplet,
    wherein the culturing is performed in said liquid droplet in a state in which a gas can be supplied to a portion immediately below said liquid droplet.

2. The method according to claim 1, wherein said water-repellent surface comprises a water-repellent layer of a compound having a hydrophobic moiety formed on the surface of said substrate.

3. The method according to claim 2, wherein a volume of said liquid droplet is at least 200 μL.

4. The method according to claim 1, wherein the biological organic material cultured in said liquid droplet is a stem cell of at least one kind and/or a cell or tissue differentiated from said stem cell.

5. The method according to claim 4, wherein said stem cell of at least one kind is cultured in said liquid droplet and said stem cell is differentiated in said liquid droplet.

6. The method according to claim 5, wherein the differentiated biological organic material derived from said stem cell is a cartilage cell and/or cartilage tissue.

7. The method according to claim 1, wherein the biological organic material is cultured in a state in which said liquid droplet is stationary disposed on said water-repellent surface.

8. The method according to claim 1, wherein the biological organic material is cultured, while continuously or intermittently moving said liquid droplet on said water-repellent surface.

9. A culture vessel for use in production of a biological organic material in a liquid droplet comprising a culture medium containing predetermined components, the culture vessel comprising:
    a liquid droplet disposition portion configured of a water-repellent surface where a substantially spherical liquid droplet can be disposed in a non-fixed state;
    a circumferential wall or partition portion provided around said liquid droplet disposition portion to prevent said liquid droplet from flowing out to the outside of said liquid droplet disposition portion; and
    a substrate formed so that a gas can be supplied immediately below a liquid droplet disposed in said liquid droplet disposition portion, wherein
    at least a surface of the substrate that can come into contact with said liquid droplet has water repellency capable of holding the liquid droplet in a substantially spherical state,
    a plurality of protruding portions arranged with a predetermined spacing and having said water-repellent surface are formed on said substrate, and
    configuration is made so that said liquid droplet is disposed on said plurality of protruding portions in a state in which the lowermost portion of said liquid droplet is floating above said substrate.

10. The culture vessel according to claim 9, wherein a volume of a liquid droplet that can be disposed on said protruding portions is at least 100 μL.

11. A culture vessel for use in production of a biological organic material in a liquid droplet comprising a culture medium containing predetermined components, the culture vessel comprising:
    a liquid droplet disposition portion configured of a water-repellent surface where a substantially spherical liquid droplet can be disposed in a non-fixed state;
    a circumferential wall or partition portion provided around said liquid droplet disposition portion to prevent said liquid droplet from flowing out to the outside of said liquid droplet disposition portion; and
    a substrate formed so that a gas can be supplied immediately below a liquid droplet disposed in said liquid droplet disposition portion, wherein
    at least a surface of the substrate that can come into contact with said liquid droplet has water repellency capable of holding the liquid droplet in a substantially spherical state,
    said substrate comprises a mesh portion having a water-repellent surface capable of holding the liquid droplet in a substantially spherical state, and
    configuration is made so that when said liquid droplet is disposed on said mesh portion, the lowermost portion of said liquid droplet is disposed in a gap portion of said mesh portion.

12. The vessel according to claim 9, wherein said water-repellent surface is configured of a water-repellent layer comprising a compound having a hydrophobic moiety.

13. The method according to claim 1, wherein said water-repellent surface comprises a water-repellent layer of a compound having a hydrophobic moiety formed on the surface of said substrate.

14. The method according to claim 1, wherein the biological organic material cultured in said liquid droplet is a stem cell of at least one kind and/or a cell or tissue differentiated from said stem cell.

15. The vessel according to claim 11, wherein
    said water-repellent surface comprises a water-repellent layer comprising a compound having a hydrophobic moiety.

16. A culture vessel for use in production of a biological organic material in a liquid droplet comprising a culture medium containing predetermined components, the culture vessel comprising:

a liquid droplet disposition portion configured of a water-repellent surface where a substantially spherical liquid droplet can be disposed in a non-fixed state;

a circumferential wall or partition portion provided around said liquid droplet disposition portion to prevent said liquid droplet from flowing out to the outside of said liquid droplet disposition portion; and a substrate formed so that a gas can be supplied immediately below a liquid droplet disposed in said liquid droplet disposition portion, wherein at least a surface of the substrate that can come into contact with said liquid droplet has water repellency capable of holding the liquid droplet in a substantially spherical state and said water-repellent surface is configured of a water-repellent layer comprising a compound having a hydrophobic moiety.

* * * * *